United States Patent [19]

Kojima et al.

[11] Patent Number: 5,073,567

[45] Date of Patent: Dec. 17, 1991

[54] ANTIPARASITIC AGENT

[75] Inventors: Yasuhiro Kojima; Hiroshi Maeda; Satoshi Nishiyama, all of Aichi, Japan; David A. Perry, Kent, England

[73] Assignee: Pfizer Inc., New York, N.Y.

[21] Appl. No.: 557,885

[22] Filed: Jul. 25, 1990

[30] Foreign Application Priority Data

Jul. 26, 1989 [GB] United Kingdom ............... 8917064

[51] Int. Cl.$^5$ .................. A61K 31/365; C07D 313/00
[52] U.S. Cl. ..................................... 514/450; 549/264
[58] Field of Search ........................ 549/264; 514/450

[56] References Cited

FOREIGN PATENT DOCUMENTS 170006 2/1986 European Pat. Off. .
254583 1/1988 European Pat. Off. .
1390336 4/1975 United Kingdom .

Primary Examiner—C. Warren Ivy
Assistant Examiner—Ba K. Trinh
Attorney, Agent, or Firm—Peter C. Richardson; J. Trevor Lumb; A. Dean Olson

[57] ABSTRACT

An antibiotic compound of the formula:

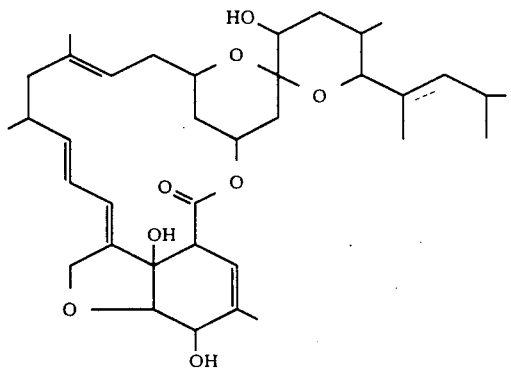

is an antiparasitic agent active against insect pests, acari, free living nematodes and endo- and ectoparasites. It is prepared by fermentation using the microorganism *Streptomyces griseochromogenes* ATCC 53928.

5 Claims, No Drawings

ANTIPARASITIC AGENT

Technical Field

This invention relates to a new antiparasitic agent and in particular to a novel macrolide related to the milbemycins, to a process for its preparation, and to compositions containing it.

BACKGROUND ART

The milbemycins form an important group of broad spectrum antiparasitic agents possessing anthelmintic, ectoparasiticidal, insecticidal, antibacterial, antifungal and growth promoting activity with application in the areas of animal and human health, agriculture and horticulture. They are produced by fermentation of certain microorganisms of the genus Streptomyces under aerobic conditions in an aqueous or solid nutrient medium containing inorganic salts and assimilable sources of carbon and nitrogen. For example, fermentation of the microorganism *Streptomyces hygroscopicus spp aureolacrimosus* B-41-146 as described in British patent specification 1390336 produces a family of milbemycins known collectively as the B-41 compounds. In another example, fermentation of *Streptomyces cyaneogriseus spp noncyanogenus* as described in European patent specification EP-A-0170006 produces another family of milbemycins known collectively as the LL-F28249 compounds.

Compounds related to the milbemycins are described in EP-A-0254583. They are obtained by fermentation of Streptomyces micro-organisms known as Streptomyces E225 and Streptomyces E225B.

SUMMARY OF THE INVENTION

We have now discovered a new macrolide designated herein as UK-86,956 which may be produced by the culture of a novel microorganism *Streptomyces griseochromogenes* N859-124 as described below. The highly active compound UK-86,956 possesses a broad spectrum of activity against insect pests, acari, free living nematodes and endo- and ectoparasites afflicting animals and humans.

Thus one aspect of the present invention provides compound UK-86,956 believed to have the formula (I):

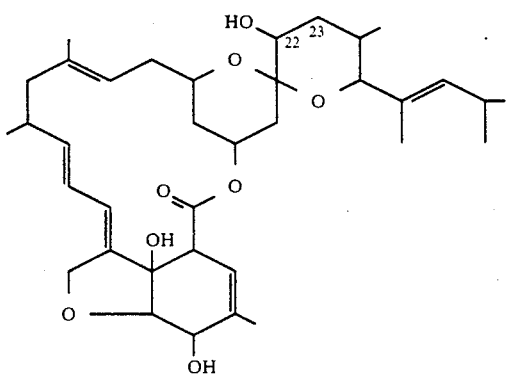

Another aspect of this invention is a compound of formula I in which the relative stereochemistry is as depicted by formula II:

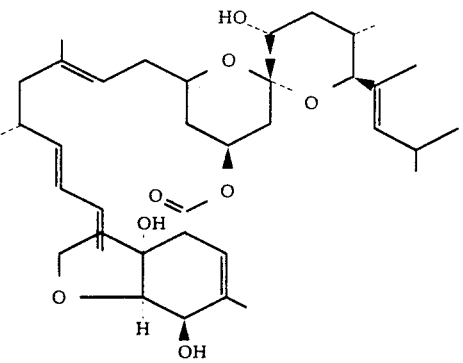

Yet another aspect of this invention is a compound preparable by fermentation of the microorganism *Streptomyces griseochromogenes* ATCC 53928, or a mutant, genetically transformed or recombinant form thereof.

Another aspect of this invention is a method for producing a compound of formula I which comprises cultivating the microorganism N859-124, or a mutant, genetically transformed or recombinant form thereof having the ability to produce said compound, in media containing an assimilable source of carbon, nitrogen and inorganic salts, under aerobic fermentation conditions until a recoverable amount of said compound is obtained.

The term mutant includes any mutant strain which arises spontaneously or by the application of known techniques, such as exposure to ionising radiation, ultraviolet light, and/or chemical mutagens such as N-methyl-N-nitroso-urethane, nitrosoguanidine and ethane methane sulphate, etc. Genetically transformed and recombinant forms include mutants and genetic variants produced by genetic engineering techniques, including for example recombination, transformation, transduction, and protoplast fusion, etc. The invention also extends to UK-86,956 produced by said process.

The present invention is also directed to compositions for the controlling of parasitic infections in humans or animals which comprises a compound as defined in claim 1 together with an inert diluent or carrier; and to a method of controlling insect or parasite infections or infestations which comprises applying an infection or infestation controlling amount of a compound of formula I to the organism responsible for the infection or infestation, or to the location thereof.

Yet another aspect of this invention is a biologically pure culture of a strain of the genus Streptomyces having the identifying characteristics of ATCC 53928, or a mutant, genetically transformed or recombinant form thereof, said microorganism being capable of producing the antibiotic compounds of formula I in recoverable quantity upon cultivation in an aqueous nutrient medium containing an assimilable source of carbon, nitrogen and inorganic salts.

The present invention is also directed to *Streptomyces griseochromogenes* ATCC 53928. UK-86,956 is distinguished from the compound LL-F28249α described in EP-A-0170006 in possessing a hydroxy substituent at the C-22 position rather than at C-23. It is also distinguished from the compounds disclosed in EP-A-0254583 in having a 1,3-dimethylbut-1-enyl radical at the 25 position instead of a 1-methylprop-1-enyl radical.

DETAILED DESCRIPTION OF THE INVENTION

UK-86.956 may be produced by the submerged aerobic fermentation in aqueous nutrient media or by a solid agar fermentation under aerobic conditions of a microorganism isolated from a soil sample collected in Itoh City, Shizuoka Prefecture, Japan. This micro-organism has been deposited in the American Type Culture Collection, 12301 Parklawn Drive, Rockville, Md. 20852, U.S.A. under accession number ATCC 53928 on 29th June 1989. It is designated herein as culture N859-124. It has been characterised as follows:

The culture N859-124 was planted from a slant into ATCC #172 broth and grown for four days at 28° C. on a shaker. It was then centrifuged for 20 minutes, washed three times with sterile water and planted on media commonly used for identification of members of the Actinomycetales.

The culture was incubated at 28° C. and the results were read at varying times but most commonly were taken at 14 days. The colors were described in common terminology, but exact colors were determined by comparisons with color chips from the *Color Harmony Manual*, fourth edition. The methods of whole-cell amino acid and sugar analyses are those described in Becker, B. et al., Appl. Microbiol., 12: 421-423, 1964; and in Lechevalier, M.P., J. Lab. Clin. Med., 71: 934-944, 1968. For comparison purposes, the type strains of *Streptomyces griseochromogenes* ATCC 14511 and S. *durhamensis* ATCC 23194 were purchased from American Type Culture Collection in Rockville, Md.

Identification media used for the characterization of the cultures and references for their composition are as follows:

1. Tryptone-Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Czapec-Sucrose Agar—S. A. Waksman, The Actinomycetes, Vol. 2, medium no. 1, p. 328, 1961.
8. Glucose-Asparagine Agar—Ibid, medium no. 2, p. 328.
9. Bennett's Agar—Ibid, medium no. 30, p. 331.
10. Emerson's Agar—Ibid, medium no 28, p. 331.
11. Nutrient Agar—Ibid, medium no. 14, p. 330.
12. Gordon and Smith's Tyrosine Agar - R. E. Gordon and M. M. Smith, J. Bacteriol. 69: 147-150, 1955.
13. Casein Agar—Ibid.
14. Calcium Malate Agar—S. A. Waksman, Bacteriol. Rev. 21: 1-29, 1957.
15. Gelatin - R. E. Gordon and J. M. Mihm, J Bacteriol. 73: 15-27, 1957.
16. Starch—Ibid
17. Organic Nitrate Broth—Ibid.
18. Dextrose Nitrate Broth—S. A. Waksman, The Actinomycetes, Vol. 2, medium no. 1, p. 328, 1961, with 3 g dextrose substituted for 30 g sucrose and agar omitted.
19. Potato Carrot Agar—M. P. Lechavalier, J. Lab. and Clinical Med. 71: 934-944, 1968, but use only 30 g potatoes, 2.5 g carrots and 20 g agar.
20. 2% Tap Water Agar.
21. Skim Milk—Difco.
22. Cellulose utilization—
    a) H. L. Jensen, Proc. Linn. Soc. N.S.W. 55: 231-248, 1930.
    b) M. Levine and H. W. Schoenlein, A Compilation of Culture Media, medium no. 2511, 1930.
23. Carbohydrate Utilization—ISP #9 medium, Difco.
24. Temperature Range—ISP #2 medium plus 50 ml per liter of coconut milk.

Yeast Extract-Malt Extract Agar—Growth good, white to pale gray (near gray series 2 ba, 3 ba), raised, smooth, aerial mycelium same as surface; reverse yellowish to yellowish brown (2 lc, 3 ic); soluble pigment yellowish (2 lc).

Oatmeal Agar—Growth moderate; gray, dark gray to pink gray (near gray series 3 dc, 3 fe, 5 fe, 5 ih, 4 ig); slightly to moderately raised smooth, aerial mycelium same as surface; reverse yellowish gray (½ gc, 1 ½ ic); soluble pigment none to cream (1½ ca).

Inorganic Salts-Starch Agar—Growth good; pale gray, gray to dark gray (near gray series 3 dc, 3 fe, 3 ih); raised, smooth, aerial mycelium same as surface; reverse pale yellowish (2 ca, 2 ea); soluble pigment cream (2 ca).

Glycerol-Asparagine Agar—Growth poor to moderate, off-white to pale yellowish (s ca, 2 ea), slightly raised, smooth or appearing as isolated colonies, aerial mycelium off-white; reverse pale yellowish (2 ea, 2 ca); no soluble pigment.

Czapek-Sucrose Agar—Growth poor moderate, cream (2 ca) with some pale whitish gray aerial mycelium (near gray series 3 dc, 3 fe), thin, smooth; reverse colorless to cream (2 ca); no soluble pigment.

Glucose-Asparagine Agar—Growth good; white, pale gray to gray (near gray series 3 dc, 3 fe 3 cb); raised, smooth, aerial mycelium same as surface; reverse yellowish (2 ga, 2 ia, 2 lc); soluble pigment pale yellowish (2 ea).

Gordon and Smith's Tyrosine Agar—Growth moderate, dark brown (3 nl), slightly raised, smooth to granular, no aerial mycelium; reverse dark brown (3 nl); soluble pigment dark brown (3 nl).

Casein Agar—Growth good, yellowish gray to orange gray (2 ie, 2 lg, 4 ie) with some white aerial mycelium toward end of streak, moderately raised, wrinkled; reverse yellowish (2 lc); soluble pigment dark brown (3 ni).

Bennett's Agar—Growth good, white to pale gray (near gray series 3 cb, 3 dc), raised, smooth but may be slightly wrinkled toward the edge, with hyaline exudate, aerial mycelium same as surface; reverse dark brown (3 li); soluble pigment brown (3 ng).

Emerson's Agar—Growth good, yellowish gray to gray (2 ni, 2 li), raised, wrinkled, no aerial mycelium; reverse dark brown (3 ni, 3 li); soluble pigment dark brown (3 nl, 3 pn).

Nutrient Agar—Growth poor to moderate, brown (3 lg), thin to slightly raised, smooth, or appearing as isolated colonies, no aerial mycelium; reverse brown (3 ie, 3 lg); soluble pigment yellowish brown (3 ic, 3 le).

Calcium Malate Agar—Growth moderate, gray to dark gray (near gray series 3 fe, 3 ih), slightly raised, smooth, aerial mycelium same as surface; reverse pale gray to gray (near gray series 3 dc, 3 fe); no soluble pigment.

Gelatin Agar—Growth moderate to good, white to yellowish brown (3 ec), moderately raised, smooth to wrinkled, no aerial mycelium; reverse yellowish (2 ga, 2 ic); soluble pigment dark yellowish (2 ne).

Starch Agar—Growth moderate to good, dark yellowish green (1½ ic, 1½ le), moderately raised, smooth to wrinkled, no aerial mycelium; reverse yellowish (2 ic); soluble pigment yellowish brown (3 pe).

Potato Carrot Agar—Growth poor to moderate; white, cream, to pale gray (2 ca, near gray series 3 cb, 3 dc), thin, smooth, with white to pale gray aerial mycelium; reverse colorless to cream (2 ca); no soluble pigment.

Tap Water Aqar—Growth poor, pale gray (near gray series 3 cb, 3 dc), thin, smooth, aerial mycelium pale gray; reverse colorless to pale gray (near gray series 3 cb, 3 dc); no soluble pigment.

Morphological Properties—The morphological observations were made on oatmeal agar after 14 days of incubation: spore mass in Gray color-series, spore chains in Section Spirales, tightly or slightly openly coiled, with up to 7 turns; 10 to 50 spores per spore chain; sporophores monopodially branched, rarely verticillately branched; spores globose, oval to elliptical, 0.9–1.3 um diam. or 1.2–1.8×0.9–1.3 um; spiny, as revealed by scanning electron microscopy.

Biochemical Properties—Melanin produced; hydrogen sulfide not produced; gelatin liquefied; starch hydrolyzed; dextrose nitrate but not organic nitrate reduced to nitrate; poor growth on Jensen's cellulose broth but no growth on Levin and Schoenlein's cellulose broth; no decomposition on both cellulose broths; clearing but no coagulation and no peptonization on milk; casein digestion positive; tyrosine digestion negative; calcium malate digestion negative. Carbohydrate utilization: glucose, arabinose, fructose, inositol, mannitol, raffinose, sucrose and xylose utilized; rhamnose not utilized.

| Temperature Relations | | | |
|---|---|---|---|
| 21° C. | 28° C. | 37° C. | 45° C. |
| Moderate Growth | Good Growth | Good Growth | No Growth |

Cell Wall Analysis—The whole-cell hydrolysates contained LL-diaminopimelic acid and glucose.

The culture N859-124 is characterized by the gray spores in mass, the positive melanin reaction, the spiral spore chains, and the spiny spores. The whole-cell hydrolysates indicate the presence of LL-daiminopimelic acid and the absence of diagnostic sugars. Glucose, arabinose, fructose, inositol, mannitol, raffinose, sucrose, xylose, but not rhamnose are utilized. Thus, the culture belongs to the genus Streptomyces.

When compared with the described species of Streptomyces, the culture N859-124 closely resembles *S. durhamensis* ATCC 23194 and *S. griseochromogenes* ATCC 14511 in cultural, morphological and biochemical properties. Accordingly, the three cultures were compared side-by-side to ascertain their relationships.

The culture N859-124 was similar to *S. durhamensis* in most of the biochemical properties. The former differs from the latter, however, in the failure to produce hydrogen sulfide, the ability to reduce dextrose nitrate to nitrite, the failure to coagulate and peptonize milk, and the failure to grow at 45-C. Some cultural differences were noted. For example, on oatmeal agar, inorganic salts-starch agar, and glucose-asparagine agar, colonies of the culture N859-124 showed a darker grayish tint. In addition, on glycerol-asparagine agar and Czapek-sucrose agar, the culture N859-124 but not *S. durhamensis* produced white and pale gray aerial mycelia, respectively.

The culture N859-124 was identical to *S. griseochromogenes* in melanin production, gelatin liquefaction, starch hydrolysis, nitrate reduction, reaction on milk, the temperature range for growth, and the pattern of carbohydrate utilisation. Trace of hydrogen sulfide was produced by S. griseochromogenes but not by N859-124. While both cultures showed similar morphologic and cultural properties, some minor cultural differences were noted. On organic salts-starch agar and glucose-asparagine agar, colonies of the culture N859-124 were gray rather than white because of sporulation. With the culture N859-124, more white to pale gray aerial mycelium was produced on Czapek-sucrose agar. The colonies of the culture N859-I24 were smooth rather than wrinkled on yeast extract-malt extract agar and were less spreading than those of S. griseochromogenes on Czapek-sucrose agar.

On the basis of the results mentioned above, the culture N859-124 is considered as a new strain of *Streptomyces griseochromogenes* Fukunaga.

Cultivation and isolation of macrolide UK-86,956 may be conducted under conditions similar to those generally employed to produce antibiotics by fermentation. Cultivation may take place in an aqueous nutrient medium containing suitable sources of carbon, nitrogen and trace elements for a period of several days under aerobic conditions at a temperature in the range of 24° to 36° C. As with the majority of fermentations the amount of UK-86,956 will vary with changing fermentation conditions especially with regard to nutrient components, aeration conditions and pH. The mycelial product is then recovered by centrifugation or filtration and extracted with acetone or methanol. The solvent extract is concentrated and the desired products are extracted into a water-immiscible organic solvent, such as methylene chloride, ethyl acetate, chloroform, butanol or methylisobutyl ketone. The solvent extract is concentrated and the crude product is further purified as necessary by chromatography. Final purification of UK 86,956 can be achieved by repeated column chromatography or using a technique such as reverse phase high performance liquid chromatography (HPLC), or by preparative thin layer chromatography.

Alternatively, cultivation may take place on agar plates of a suitable medium under aerobic conditions at a temperature in the range of 24° to 36° C. for several days. The agar with the mycelial growth is then extracted with an organic solvent such as methanol, filtered and the filtrate concentrated. Further enrichment and separation of UK-86,956 is then carried out as described above.

As previously mentioned the compound of the invention is a highly active, broad spectrum antiparasitic agent having particular utility as an anthelmintic, ectoparasiticide, insecticide, acaricide and animal growth promotant.

Thus UK-86,956 is effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compound is also effective against other nematodes which affect various species of animals including, for example, Dirofilaria in dogs and various parasites which can infect humans including gastrointestinal parasites such as Ancylostoma, Necator, Ascaris Strongyloides, Trichinella, Capillaria, Trichuris, Enterobius and parasites which are found in the blood or other tissues and organs such as filiarial worms and the extra intestinal stages of Strongyloides and Trichinella.

The compound is also of value in treating ectoparasite infections including in particular arthropod ectoparasites of animals and birds such as ticks, mites, lice, fleas, blowfly, biting insects and migrating dipterous larvae which can affect cattle and horses.

The compound is also an insecticide active against household pests such as the cockroach, clothes moth, carpet beetle and the housefly as well as being useful against insect pests of stored grain and of agricultural plants such as spider mites, aphids, caterpillars and against migratory orthopterans such as locusts.

The compound UK-86,956 may be administered as a formulation appropriate to the specific use envisaged and to the particular species of host animal being treated and the parasite or insect involved. For use as an anthelmintic the compound is preferably administered by injection, either subcutaneously or intramuscularly, alternatively it may be administered as a pour-on or orally in the form of a capsule, bolus, tablet or liquid drench, or may be administered as an implant. Pour-on and injection formulations are prepared in a conventional manner in accordance with standard veterinary practice. Capsules, boluses or tablets may be prepared by mixing the active ingredient with a suitable finely divided diluent or carrier, additionally containing a disintegrating agent and/or binder such as starch,lactose, talc, or magnesium stearate. A drench formulation may be prepared by dispersing the active ingredient in an aqueous solution together with dispersing or wetting agents and injectable formulations may be prepared in the form of a sterile solution or emulsion. These formulations will vary with regard to the weight of active compound depending on the species of host animal to be treated, the severity and type of infection and the body weight of the host. Generally for oral administration a dose of from about 0.001 to 10 mg per Kg of animal body weight given as a single dose or in divided doses for a period of from 1 to 5 days will be satisfactory but of course there can be instances where higher or lower dosage ranges are indicated and such are within the scope of this invention.

As an alternative the compound may be administered with the animal feedstuff and for this purpose a concentrated feed additive or premix may be prepared for mixing with the normal animal feed.

For use as an insecticide and for treating agricultural pests the compound is applied as sprays, dusts, pour-on formulations, emulsions and the like in accordance with standard agricultural practice.

For use as a growth promotant or for improving the lean meat to fat ratio in farm or domestic animals, the compound may be administered with the animal feedstuff or drinking water. Alternatively it may be administered orally in the form of a capsule, bolus, tablet or liquid drench, or parenterally by injection or as an implant. Such formulations are prepared in a conventional manner in accordance with standard veterinary practice.

For human use the compound is administered as a pharmaceutically acceptable formulation in accordance with normal medical practice.

The invention is illustrated by the following Examples in which Example 1 describes the preparation, isolation and identification of UK-86,956. Example 2 describes the anthelmintic activity of UK-86,956 and Example 3 describes the insecticidal activity of UK-86,956.

In Example 1, Oxoid peptone and Oxoid Lab Lemco were supplied by Oxoid Limited, Wade Road, Basingstoke, Hampshire, U.K.

Ultraviolet spectra were recorded using a Hewlett Packard 8452A diode array spectrophotometer.

Electron impact mass spectroscopy was performed using a VG model 7070F mass spectrometer.

Fast atom bombardment mass spectroscopy was performed using a VG model 7070E mass spectrometer. Samples were introduced using a matrix consisting of glycerol, thioglycerol, sodium chloride and water.

Optical rotation was determined on a Perkin Elmer 141 Polarimeter.

Nuclear magnetic resonance spectral data were obtained using a General Electric GN500 spectrometer.

EXAMPLE 1

The microorganism Streptomyces griseochromogenes N859-124 (ATCC 53928) was grown at 28° C. on an agar slant of the following composition: Starch 20 g/l, glucose 10 g/l, Bacto-casitone (supplied by Difco Co., Detroit, U.S.A.) 5 g/l, Difco Yeast Extract 5 g/l calcium carbonate 1 g/l, agar 20 g/l adjusted to pH 7.1. After seven days the aerial growth was used to inoculate six 500 ml Erlenmeyer flasks each containing 100 ml of a medium of the following composition: Starch 24 g/l, Oxoid Peptone 5 gl, Oxoid Yeast Extract 5 g/l calcium carbonate 4 g/l Lab Lemco 3 g/l and glucose 1 g/l. These flasks were incubated at 28° C. on a rotary shaker operating at 200 rpm for 4 days. 5 ml of this inoculum was then added to the surface of each of 117 agar plates (245×245 mm, Nunc) containing 250 ml of a medium comprising soyabean flour 10 g/l, cerelose 10 g/l starch 10 g/l, Distillers solubles 5 g/l, sodium chloride 5 g/l, calcium carbonate 1 g/l, cobalt chloride 10 mg/l and agar 20 g/l adjusted to pH 7.2. These plates were incubated at 28° C. for between 5 and 7 days before extracting all the material with methanol (30 l). The resulting suspension was filtered and concentrated under vacuum to give 1 l of aqueous solution. This was extracted three times with 1 l of ethyl acetate and the organic solution was concentrated to dryness. To the residue was added 10 ml methanol and this solution was applied to a Sephadex LH 20 column (4×85 cm) (Pharmacia) and eluted with 2 l methanol. The solvent was evaporated under vacuum and the residue chromatographed on a silica column (Kieselgel 60, 70-230 mesh, Merck) (4.5×30 cm) eluting initially with chloroform (500 ml) and finally with chloroform-ethyl acetate 20:1 (500 ml). Fractions containing UK-86,956 as determined by thin layer chromatography were concentrated to dryness under vacuum. Final purification was achieved by preparative silica layer chromatography, developing with chloroform-ethyl acetate 3:1 to yield pure UK-86,956, 64 mg.

The pure sample of UK-86,956 thus obtained possesses the following characteristic physical and spectroscopic properties:

a) Specific optical rotation $[\alpha]^{25} + 95.0°$ (c=0.16, acetone).
b) Ultraviolet absorption spectrum 238 (=24,600), max 244 (=27,000), 252(sh)(=17,500).
c) Principal ions in the electron impact mass spectrum 612 (M+), 594 (M-H$_2$O), 576 (M—2H$_2$O)+, 466, 151.
d) FAB—mass spectrum 635 (M+Na+) (Theoretical 635),
e) Proton magnetic resonance spectrum (CDCl3) in part: well resolved signals at δ=5.79 (dm, J=11.4, 1H), 5.73 (dd, J=13.8, 11.4, 1H), 5.41 (bs, 1H), 5.12 (d, J=8.1, 1H), 4.69 (dd, J=14.3, 2.1, 1H), 4.65 (dd, J=14.3, 2.1, 1H), 4.29 (m, 1H), 3.95 (d, J=6.2, 1H), 3.36 (d, J=10.2, 1H), 3.26 (m, J=2.3, 1H), 2.56 (m, 1H), 1.87 (bs, 3H), 1.57 (bs, 3H), 1.54 (bs, 2H), 1.40 (q, J=12, 1H), 1.03 (d, J=6.6, 3H), 1.00 (d, J=6.6, 3H), 0.93 (d, J=6.7, 3H), 0.70 (d, J=6.6, 3H).

By detailed analysis of the nuclear magnetic resonance data the compound obtained is believed to have the following relative stereochemistry:

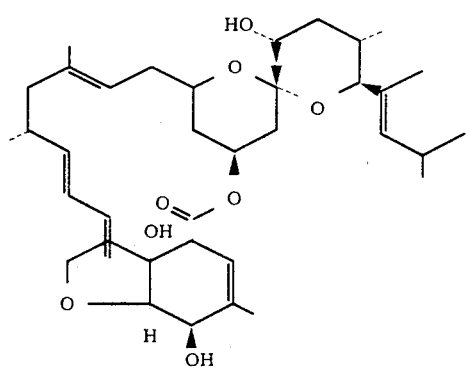
(II)

EXAMPLE 2

Anthelmintic activity of the compound UK-86,956 obtained as in Example 1 was evaluated against *Caenorhabditis elegans* using the in vitro screening test described by K. G. Simpkin and G. L. Coles in Parasitology, 1979, 79, 19. The compound killed 100% of the worms at a well concentration of 0.01 parts per million.

EXAMPLE 3

Insecticidal activity of UK-86,956 was evaluated against the larval stage of the blowfly *Lucilia cuprina* (Q strain) using a standard procedure in which first instar larvae are kept in contact with filter paper treated with test compound. The test compound is first applied to the paper as an acetone solution. The treated filter paper is then placed into a tube containing 1 ml of newborn calf serum and the first instars are added. UK-86,956 killed 100% of the larvae when applied to the filter paper at a level of 10 mg per square meter.

We claim:

1. A compound having the formula:

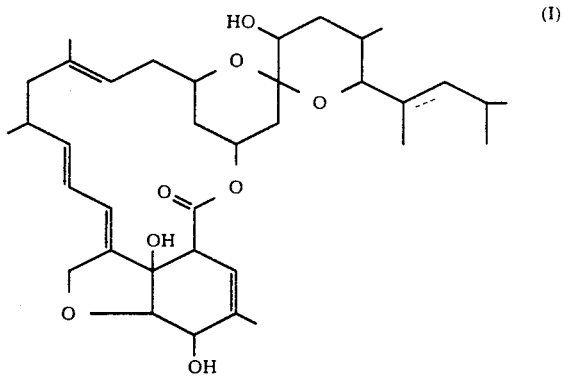
(I)

2. A compound of formula (I) in which the relative stereochemistry is as depicted by formula (II):

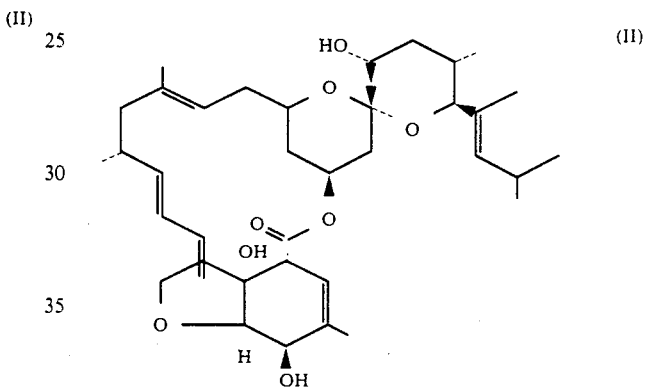
(II)

3. A composition for the treatment or prevention of parasitic infections in humans or animals, including anthelmintic, insecticidal and aracidal compositions, which comprises a compound as defined in claim 1 together with an inert diluent or carrier.

4. A composition as claimed in claim 3 in the form of an oral, injectable or pour-on formulation, or in the form of a spray or dust, or in the form of a concentrated feed additive premix or supplement for incorporation with the normal animal feed.

5. A method of combatting insect or parasite infections or infestations, including parasitic conditions in humans and animals, and agricultural or horticultural pest infestations, which comprises applying an infection or infestation controlling amount of a compound as defined in claim 1 to the organism responsible for the said infection or infestation, or to the location thereof.

* * * * *